United States Patent [19]

Henderson et al.

[11] Patent Number: 5,486,569
[45] Date of Patent: Jan. 23, 1996

[54] METHOD OF INCREASING THE SIZE AND/OR ABSORPTION UNDER LOAD OF SUPERABSORBENT POLYMERS BY SURFACE CROSS-LINKING AND SUBSEQUENT AGGLOMERATION OF UNDERSIZED PARTICLES

[75] Inventors: John A. Henderson, Birkenhead, United Kingdom; Anthony S. Tomlin, Island Lake, Ill.; David M. Lucas, West Kirby, United Kingdom

[73] Assignee: American Colloid Company, Arlington Heights, Ill.

[21] Appl. No.: 314,363

[22] Filed: Sep. 28, 1994

[51] Int. Cl.$^6$ .................................................. C08F 8/32
[52] U.S. Cl. ...................... 525/116; 525/119; 525/324.9; 525/330.1; 525/382; 525/383; 525/304
[58] Field of Search ................................. 525/116, 119, 525/382, 383, 384

[56] References Cited

U.S. PATENT DOCUMENTS

| | | | |
|---|---|---|---|
| 4,541,871 | 9/1985 | Obayashi et al. | 106/197.2 |
| 4,587,308 | 5/1986 | Makita et al. | 525/373 |
| 4,732,968 | 3/1988 | Obayashi et al. | 528/490 |
| 5,149,335 | 9/1992 | Kellenberger et al. | 604/372 |

FOREIGN PATENT DOCUMENTS

| | | |
|---|---|---|
| 0224923A2 | 10/1987 | European Pat. Off. . |
| 0450923A2 | 9/1991 | European Pat. Off. . |
| 0450924A2 | 9/1991 | European Pat. Off. . |
| 0463388A1 | 2/1992 | European Pat. Off. . |
| 57-117551 | 7/1982 | Japan . |
| 2162525 | 5/1986 | United Kingdom . |
| WO90/08789 | 9/1990 | WIPO . |

*Primary Examiner*—Bernard Lipman
*Attorney, Agent, or Firm*—Marshall, O'Toole, Gerstein, Murray & Borun

[57] ABSTRACT

A method of enhancing the water or aqueous fluid absorption of and/or increasing the particle size of fine water-absorbent polyacrylic SAP polymer particles includes surface-contacting the SAP polymer particles with a solution containing a cross-linking agent for the polyacrylic SAP polymer, and then subjecting the particles to conditions sufficient to further cross-link the surfaces of the SAP polymer particles. The surface cross-linked particles are then impregnated with water in a weight ratio of SAP polymer, dry basis, to water in the range of about 1:1 to about 1:10 to form a paste, and the paste is subjected to conditions, such as increased temperature, e.g., 50° C.–150° C. to dry the polymer particles to form an acrylic SAP polymer having enhanced fluid absorption under load and, upon pulverizing, increased particle size.

27 Claims, No Drawings

METHOD OF INCREASING THE SIZE AND/OR ABSORPTION UNDER LOAD OF SUPERABSORBENT POLYMERS BY SURFACE CROSS-LINKING AND SUBSEQUENT AGGLOMERATION OF UNDERSIZED PARTICLES

FIELD OF THE INVENTION

The present invention relates to a method of increasing the size and absorption under load of particles of polyacrylic superabsorbent polymer (SAP) by surface cross-linking the particles, followed by intimately mixing the fine particles, with water, into a high viscosity paste for continued cross-linking and drying. The paste then is subjected to conditions suitable to dry the particle surfaces sufficiently, such as by subjecting the paste to extrusion and elevated temperature so that the product may be milled to a desired particle size range containing particles greater in size than the original fine material (dry agglomeration). The so-formed agglomerates surprisingly remain as single particles upon hydration with saline (wet agglomeration) and display improved absorption under an applied load (AUL).

BACKGROUND OF THE INVENTION AND PRIOR ART

Water-absorbing resins have found wide use in sanitary goods, hygenic goods, wiping cloths, water retaining agents, dehydrating agents, sludge coagulants, disposable towels and bath mats, disposable door mats, thickening agents, disposable litter mats for pets, condensation preventing agents and release control agents for various chemicals. Water-absorbing resins are available in a variety of chemical forms including substituted and unsubstituted natural and synthetic polymers such as hydrolysis products of starch acrylonitrile graft polymers, carboxymethylcellulose, cross-linked polyacrylates, sulfonated polystyrenes, hydrolyzed polyacrylamides, polyvinyl alcohols, polyethylene oxides, polyvinylpyrrolidines and polyacrylonitriles.

In some polymerization processes for manufacturing water-absorbent polymers, such as cross-linked polyacrylic super-absorbent polymers, e.g., polyacrylic acid, or partially neutralized or fully neutralized polyacrylic acid, one or more monomers are polymerized in water to produce a polymer that then must be ground to provide a desired particle size, with or without an intermediate drying step, for incorporation into a variety of different products, as outlined above. During the grinding process, fine particles result that are undesirable due to dusting problems, or other manufacturing problems. Fine superabsorbent material is considered to be undesirable in many personal care applications including infant diapers and adult incontinence devices. Such fine material can migrate in the device before use and exhibit gel blocking in application.

European Patent EP 0 463 388 A1 (Hoescht Celanese) discloses a process for recycling sub 75 μm SAP fines back into a reaction gel at 16%–17% solids. However, only 4% recycle is possible and the addition of extra process water is required. International classification CO8L33/02 (Seitetsu) describes a method whereby fine powder may be blended with a prepared polyacrylate solution into a crumbly mix which generates agglomerates on drying at up to 150° C. International publication number WO 90/08789 (Dow) describes an agglomeration route involving the use of hydrocarbon solvents to suspend fine particles which are then clustered by the addition of acrylate monomer solution under polymerization conditions in the presence of an amorphous silica powder. Seitetsu also disclose the use of organic solvents as a dispersion phase in U.S. Pat. No. 4,732,968 (EP 0 224 923). SAP fines are dispersed in an inert solvent with addition of silica in the presence of water and a suitable surfactant, followed by removal of solvent and drying.

All the above disclosures share disadvantages of either relatively low rates of fines consumption, or the use of large amounts of organic solvents and expensive silica additives. In addition there is no claim of enhanced superabsorbent performance other than lack of gel blocking in the agglomerated material.

In the present invention, a preferred process is disclosed wherein fine SAP particles are surface treated with an aqueous solution of cross-linking agent, preferably applied as a fine mist to freely tumbling SAP particles. The surface coated particles then are subjected to an elevated temperature, in order to increase the reaction rate of the surface cross-linking reaction, and to dry the coated particles to a moisture content of about 15% by weight or less. In the preferred embodiment, to achieve an increased particle size, the dried product of this surface cross-linking stage then is mixed intimately with a suitable amount of water, e.g., in a high shear mixer, such as a Z-blade mixer or Sigma blender, in order to achieve a continuous paste. Preferably, the paste is subjected to conditions which simultaneously promote drying of the paste particles. Upon subsequent milling of the dry product (0 to about 15% by weight water based on the dry weight of the polymer), particles of increased particle size are obtained. These particles retain particle integrity upon hydration and demonstrate enhanced polymer performance in the absorption under load test, described in more detail hereinafter.

SUMMARY OF THE INVENTION

In brief, the present invention is directed to a process of increasing the size of fine particles of a superabsorbent polymer (SAP) selected from cross-linked polyacrylic acid; cross-linked, partially neutralized polyacrylic acid; cross-linked, fully neutralized polyacrylic acid; and mixtures thereof and, more particularly, to a process of surface treating (at least partially "coating") the SAP with a cross-linking agent for polyacrylic acid and/or metal salts of polyacrylic acid, followed by intimate mixing of the surface cross-linked polymer with water, such as in a suitable high shear mixer.

In a preferred embodiment, surface cross-linking is achieved by spraying the SAP fines with an aqueous solution of the cross-linking agent to wet predominantly only the outer surfaces of the SAP particles. Cross-linking and drying of the polymer then is achieved, preferably by heating at least the wetted surfaces of the SAP particles. The dry (15% by weight, or less, water), surface cross-linked polymer preferably then is mixed with water, e.g., under high shear, in order to produce a continuous paste. In a preferred embodiment, this paste then is extruded or otherwise discharged from the mixer and dried so as to produce a brittle "crumb" product. The dry "crumb" product then is milled to a suitable particle size distribution, to yield a product of improved particle size distribution (hereinafter defined as dry agglomeration), which retains its agglomerated nature upon hydration (hereinafter defined as wet agglomeration) and displays improved absorption under load (AUL) when compared to the original fine SAP material.

In accordance with the present invention, the fine particles of SAP are surface treated with an aqueous solution of cross-linking agent for the SAP. The solution contains from about 0.01% to about 4% w/w cross-linking agent, preferably about 0.4% to about 2% w/w cross-linking agent. In the preferred embodiment, the solution is applied to the fine SAP particles as a fine spray to the surface of freely tumbling SAP particles at a ratio of about 1:0.01 to about 1:0.5 parts by weight polymer fines to solution of cross-linking agent, preferably about 1:0.05 to about 1:0.2 parts by weight polymer fines to solution of cross-linking agent.

The cross-linking reaction and drying of the polymer preferably are achieved by heating the polymer at a suitable temperature, e.g., 50° C.–150° C., preferably about 105° C. to about 120° C. It is understood, however, that any other method of reacting the cross-linking agent to achieve surface cross-linking of the SAP polymer fines, and any other method of drying the SAP fines, such as using microwave energy, or the like, are suitable in accordance with the present invention.

In a preferred embodiment of the invention, the surface-treated polymer then is further treated by intimate, high shear mixing with water. The water is impregnated completely into the particles at a weight ratio of polymer to water in the range of about 1:1 to about 1:10, preferably about 1:1 to about 1:5, more preferably about 1:1 to about 1:3, in a suitable mixer, e.g., a high shear mixer, to form a continuous paste. The paste mixture of fines and water should have a consistency of a relatively stiff dough or paste, and the mixing should be sufficiently thorough that the particle memory of the original fines are lost and the water thoroughly penetrates the fines. Suitable mixers include Z-blade or Sigma blade mixers, planetary mixers, or other mixers designed to process high viscosity mixes.

In accordance with a preferred embodiment of the present invention, the formed paste is conveniently rendered suitable for drying and/or cross-linking by extrusion into strands, which are then subjected to sufficient temperature, e.g., in the range of about 50° C. to about 150° C., preferably about 105° C. to about 120° C., such that the dried polymer is sufficiently brittle to mill or otherwise pulverize into a desired particle size distribution (e.g., a water content of about 0 to about 15% by weight water, based on the dry weight of the polymer).

To achieve the full advantage of the present invention the combination of water and fines that forms the paste should be of a consistency to retain a hand molded shape or retain a strand structure upon extrusion. Such SAP pastes are not too soft to prevent efficient processing, nor so stiff as to damage the product through excessive shearing during mixing.

One aspect of the present invention is to provide a process for increasing the size of cross-linked SAP particles by surface treating (at least partially coating) the fine particles with an aqueous solution of cross-linking agent; surface cross-linking and drying the polymer particles; and, mixing the thus treated surface cross-linked and dried fine SAP particles with water to form a paste—thereby causing individual particle memory to be lost. Thus, on subsequent drying and milling, a SAP powder fraction is obtained of increased particle size and water-absorbing performance.

The coating solution should contain from about 0.01% to about 4% w/w cross-linking agent, preferably about 0.4% to about 2% w/w cross-linking agent. In the preferred embodiment, the solution of cross-linking agent is applied to the SAP fine particles as a fine spray to the surface of the SAP particles at a weight ratio of about 1:0.01 to about 1:0.5 parts polymer to solution, preferably about 1:0.05 to about 1:0.2 parts polymer to solution. In the preferred embodiment, water then is thoroughly impregnated into the surface cross-linked particles to form a paste at a weight ratio of polymer to water in the range of about 1:1 to about 1:10, preferably about 1:1 to about 1:5, and more preferably about 1:1 to about 1:3.

In the preferred embodiment, fine particles of water-absorbing, cross-linked acrylic resin are increased in size and water-absorbing capability by surface coating the relatively fine particles of acrylic resin with a solution containing a cross-linking agent for the SAP, and then intimately mixing dried (less than about 15% by weight water, based on the dry weight of the polymer), surface cross-linked particles with water to form a paste, thereby removing the original fine particle memory, followed by drying and pulverizing.

The solid resin particles, prior to surface contact with the solution of cross-linking agent, preferably have a particle size less than about 300 μm. The fine particles of the cross-linked, polyacrylic, water-absorbent polymer can be initially manufactured by any process and such fine, cross-linked polyacrylic polymer particles can have their size increased in accordance with the method of the present invention. The resulting increased size polymer particles display wet agglomeration and improved absorption under load upon hydration.

The above and other aspects and advantages of the present invention will become apparent from the following detailed description of the preferred embodiments.

DETAILED DESCRIPTION OF THE PREFERRED EMBODIMENT

In accordance with the preferred embodiment of the present invention, improved polyacrylic SAP particles, having increased particle size (dry agglomeration), retained particle integrity upon hydration (wet agglomeration) and increased absorption under load are prepared by initially surface-contacting, or at least partially coating, fine solid SAP polymer particles of a cross-linked, water-absorbent acrylic polymer with an aqueous solution of a cross-linking agent for the polymer. Suitable cross-linked polyacrylic SAP polymers include polyacrylic acid, partially neutralized polyacrylic acid, fully neutralized polyacrylic acid, and mixtures thereof. The solution of cross-linking agent should contain about 0.01% to about 4% w/w cross-linking agent, preferably about 0.4% to about 2% w/w cross-linking agent. Preferably, the solution is applied as a fine spray to the surface of the SAP particles at a weight ratio of about 1:0.01 to about 1:0.5 parts polymer to solution, preferably about 1:0.05 to about 1:0.2 parts polymer to solution of cross-linking agent. In the preferred embodiment, cross-linking of the surface of the polymer particles and drying of the particles is achieved by heating the polymer at a temperature in the range of about 105° C. to about 120° C. for a sufficient time to ensure complete reaction of the surface-applied cross-linking agent and drying, (e.g., 0 to about 15% by weight water remaining, based on the dry weight of the polymer), e.g., for about one hour.

Suitable cross-linking agents include the di- or polyfunctional molecules capable of cross-linking polyacrylic acid and/or metals salts of polyacrylic acid by reaction with the acrylic or acrylate functional groups of the polymer. Such cross-linking agents include diglycidyl ethers, dialcohols, and diamines. Preferably, the cross-linking agent should be water-soluble and possess reactivity with the polymer such that cross-linking occurs in a controlled fashion in the temperature range of about 50° C. to about 150° C. Suitable cross-linking agents include ethylene glycol, polyethylene glycols, polypropylene glycols, and diglycidyl ethers of (poly) ethylene glycols. Of particular preference is ethylene glycol diglycidyl ether (EGDGE), a water-soluble diglycidyl ether which cures with (cross-links) polyacrylate SAP polymer particles in the temperature range of about 50° C. to about 150° C.

After surface cross-linking, in the preferred embodiment, the coated fine particles are subsequently subjected to intimate mixing with water in order to thoroughly and homogeneously wet, expand and soften the particles, so that the mix attains the consistency of a dough or paste. The weight ratio of polymer particles to water should be in the range of about 1:1 to about 1:10, preferably about 1:1 to about 1:5, more preferably about 1:1 to about 1:3 to provide a dough or paste of suitable consistency. The dough or paste then is subjected to conditions sufficient to dry the polymer, preferably drying by heating at a temperature in the range of about 50° C. to about 150° C., and more preferably about 105° C. to about 120° C.

The SAP particles to be agglomerated preferably have a particle size less than about 300 µm, prior to surface contact with the cross-linking agent-containing solution, to enlarge the particles and improve their water-absorbency properties. It is understood, however, that the process of the present invention is also useful to improve the absorbency properties of acrylic, water-absorbent polymers regardless of their size. Surface cross-linking of fine SAP particles, followed by thorough mixing with water to form a continuous paste, drying and milling results in an increase in the size of the particles, without particle number increase upon hydration, and enhanced absorption properties, as measured by the absorption under load test, described in more detail hereinafter.

Surface coating of SAP fines with an aqueous solution of cross-linking agent may be achieved by spraying the solution onto the particles in the form of a fine mist while the particles are allowed to tumble freely in a drum coater. The coated particles then are subjected to conditions sufficient for reacting the cross-linking agent with the surface of the SAP particles. The following process step of intimately mixing the surface cross-linked SAP particles with water preferably is achieved by mixing the SAP particles with water in a suitable high shear mixer, such as a Z-blade mixer or Sigma blender, to form a dough or paste. For the purposes of drying the paste or dough, it is preferable that the paste or dough is subdivided into smaller masses, for example by extrusion through die openings of about 4 mm–6 mm in diameter to achieve drying to a moisture content suitable for pulverizing (e.g., less than about 15% by weight water) within a reasonable period of time, e.g., about 1 hour.

After the drying step, the solid polymer strands may be milled easily to a required particle size distribution, by the usual methods, for example by milling or pulverizing. Any resulting fines can be treated again in accordance with the method of the present invention so there are essentially no wasted fine particles.

Dry Agglomeration

Dry agglomeration is defined as a change in particle size distribution of a dry agglomerated powder fraction towards larger particle sizes than the original fines powder fraction. Dry agglomeration was determined by shaking samples over a standard, 300 µm mesh, screen (U.S. Sieve Series No. 50) and measuring the percentage retention on the screen. Fine SAP particles used to prepare agglomerates were sized to less than 300 µm before Use.

Wet Agglomeration

Wet agglomeration is defined as the ability of an SAP agglomerate to retain its single particle nature upon hydration, i.e., a lack of deagglomeration upon hydration. Wet agglomeration was determined by weighing out 50 agglomerate particles on a watch glass and hydrating them with 20 times their weight in 1% sodium chloride solution (1% saline). The particles were allowed to absorb the saline solution for one hour and then the number of particles was recounted under a microscope.

Absorption Under Load

Absorption under load (AUL) is a measure of the ability of a superabsorbent to absorb fluid under an applied pressure. The AUL was determined by the following method as disclosed in European Pat. No. 443,627 and corresponding U.S. Pat. No. 5,149,335, hereby incorporated by reference.

0.16 g +/−0.001 g of SAP is carefully scattered onto a 140 µm water-permeable mesh attached to the base of a hollow plexiglass cylinder with an internal diameter of 25 mm. The sample is covered with a 100 g cover plate and the cylinder assembly weighed. This gives an applied pressure of 20 $g/cm^2$. The screened base of the cylinder is placed in 100 mm petri dish containing 25 mls of 1% saline, and the polymer is allowed to absorb for 1 hour. By reweighing the cylinder assembly the AUL may be calculated by dividing the weight of liquid absorbed by the weight by dry weight of polymer before liquid contact.

The present invention is described in greater detail with reference to the following examples.

EXAMPLE 1

Sodium polyacrylate fines (<300 µm) were coated with a 1.2% by weight aqueous solution of diepoxy cross-linking agent, ethylene glycol diglycidyl ether (DENACOL-810, Nagase Chem. Co.) in a rotating drum coater by applying the solution to the freely tumbling particles as a finely misted spray. A weight ratio of 1:0.1 parts polymer to coating solution was employed. After coating, the polymer was heated at 120° C. for one hour to react the cross-linking agent with the surface of the polymer particles, and dry the polymer particles.

To 70 parts by weight water in the chamber of a Winkworth Model 14Z Z-blade mixer/extruder (Winkworth Ltd., Reading, UK), was gradually added 30 parts by weight (dry basis) of the dried coated superabsorbent polymer fines, having a particle size less than 300 µm). Mixing was extended for five minutes until the polymer and liquid were thoroughly mixed. The resultant high viscosity paste was extruded through a mincer head die plate with 4 mm apertures and the extruded paste then was laid flat upon perforated trays. The extrudate was dried for one hour at 120° C. in a forced air oven, until sufficiently brittle to mill (about 10% by weight water, dry basis).

The brittle product was milled to a powder fraction and sized between 300 µm and 850 µm (on-size). 43% of the product was found to be on size. Upon hydration of 50 counted particles of this product, recounting gave 49 particles, indicating successful wet agglomeration. The AUL at 0.28 psi was found to be 23.2 g/g.

EXAMPLE 2

The procedure of Example 1 was followed except that the ratio of fine particles to water in the Z-blade chamber was altered to 40 parts solid to 60 parts liquid. Upon milling of the dried extrudate, 52% was sized between 300 µm and 850

μm. Hydration of 50 on-size agglomerates yielded 50 hydrated particles and an AUL of 23.3 g/g was obtained.

Comparative Example 1

For comparison, the fine superabsorbent material used to prepare the agglomerates of Examples 1 and 2 was found to have an absorption under load of 9.0 g/g.

Comparative Example 2

The fine superabsorbent material used previously was treated by the surface treatment method of Example 1, but not subject to further treatment. Dry sizing gave 35% between 300 μm and 850 μm, and the absorption under load was found to be 22.1 g/g. Hydration of 50 on-size particles yielded a wet particle size count of 420 particles, indicating failure of the wet agglomeration test.

It should be understood that the above examples are provided for the purposes of illustration, and are not intended to limit the scope of the invention. A variety of embodiments will be evident to those skilled in the art.

It will be understood that the present disclosure has been made only by way of preferred embodiments and that numerous changes in details of construction, combination, and arrangement of parts can be resorted to without departing from the spirit and scope of the invention as hereunder claimed.

What is claimed is:

1. A method of enhancing the water or aqueous medium absorbance and particle size of water-absorbent, cross-linked polyacrylic polymer particles selected from the group consisting of polyacrylic acid; partially neutralized polyacrylic acid; fully neutralized polyacrylic acid; and mixtures thereof comprising:

contacting the surface of the polyacrylic polymer particles with a solution containing a polyfunctional cross-linking agent capable of cross-linking said polyacrylic polymer;

wherein the solution is surface coated onto the cross-linked polyacrylic polymer particles in a weight ratio of polyacrylic polymer, dry basis, to coating solution in the range of about 1:0.01 to about 1:0.5;

subjecting the coated polyacrylic polymer particles to conditions sufficient to react the cross-linking agent with the surface of the polyacrylic polymer particles to form a polyacrylic polymer having enhanced water absorbance; and mixing the polyacrylic polymer particles with water, after reaction of the surface of the polyacrylic polymer particles with the cross-linking agent, in a weight ratio of polymer particles, dry basis, to water in the range of about 1:1 to about 1:10 to form a paste; drying the paste to a moisture content less than about 15% by weight; and pulverizing the dried paste to form polyacrylic polymer particles having a size greater than the size of the particles prior to the surface cross-linking reaction.

2. A method according to claim 1, wherein the weight ratio of polyacrylic polymer to cross-linking agent-containing impregnating solution is in the range of about 1:0.05 to about 1:0.2.

3. A method according to claim 1, wherein the polyacrylic polymer particles containing cross-linking agent on their surfaces are heated to a temperature sufficient to cross-link the surface of adjacent polyacrylic polymer particles, and to dry the particles to a moisture content of about 15% by weight or less, based on the dry weight of the polymer particles.

4. A method according to claim 3, wherein the polyacrylic polymer paste is dried to a degree sufficient to form a polyacrylic polymer sufficiently brittle to be pulverized.

5. A method according to claim 4, wherein the cross-linking agent surface-contacted polyacrylic polymer particles are heated to a temperature of at least about 50° C. to react the cross-linking agent with the surface of the polymer particles.

6. A method according to claim 5, wherein the cross-linking agent surface-contacted polyacrylic polymer particles are heated to a temperature of about 50° C. to about 150° C. to react the cross-linking agent with the surface of the polymer particles.

7. A method according to claim 6, wherein the cross-linking agent surface-contacted polyacrylic polymer particles are heated to a temperature of about 105° C. to about 120° C. to react the cross-linking agent with the surface of the polymer particles.

8. A method according to claim 7, wherein the cross-linking agent surface-contacted polyacrylic polymer particles are heated to a temperature of about 120° C. to react the cross-linking agent with the surface of the polymer particles.

9. A method according to claim 1, wherein the polyacrylic polymer particles, prior to surface contact with the solution of cross-linking agent, have a size less than about 300 μm.

10. A method according to claim 1, further including the step of pulverizing the polyacrylic polymer to a desired particle size distribution after reaction of the cross-linking agent on the surface of the polyacrylic polymer particles.

11. A method according to claim 1, wherein after drying the paste to a degree sufficient for pulverizing, and after pulverizing the dried paste, the polyacrylic polymer particles have a size greater than the particle size prior to contact of the particles with the solution of cross-linking agent.

12. A method according to claim 10 further including the steps of collecting fine cross-linked polyacrylic polymer particles resulting from the pulverizing step that have a size below about 300 μm, contacting the surface of the fine polyacrylic polymer particles with a solution containing a cross-linking agent for the polyacrylic polymer fines;

wherein the solution is surface coated onto the cross-linked polyacrylic polymer particles in a weight ratio of polyacrylic polymer, dry basis, to coating solution in the range of about 1:0.01 to about 1:0.5; and subjecting the coated polyacrylic polymer particles to conditions sufficient to react the cross-linking agent with the surface of the polyacrylic polymer particles to form a polyacrylic polymer having enhanced water absorbance.

13. A method according to claim 1, wherein the solution of cross-linking agent is an aqueous solution.

14. A method according to claim 1, wherein the solution of cross-linking agent comprises about 0.005% to about 4% by weight cross-linking agent, based on the total weight of the solution of cross-linking agent.

15. A method according to claim 14, wherein the solution of cross-linking agent comprises about 0.01% to about 4% by weight cross-linking agent.

16. A method according to claim 15, wherein the solution of cross-linking agent comprises about 0.4% to about 2% by weight cross-linking agent.

17. A method according to claim 13, wherein the solution of cross-linking agent comprises the cross-linking agent dissolved in a carrier consisting essentially of water.

18. A method according to claim 1, wherein the cross-linking agent is selected from the group consisting of polyglycidyl ether, polyols, polyamines and mixtures thereof.

19. A method according to claim 1, wherein the cross-linking agent is ethylene glycol diglycidyl ether.

20. A method according to claim 1, wherein the impregnated polyacrylic polymer particles surface contacted with the solution of cross-linking agent are heated to a temperature sufficient to further cross-link molecules of the polyacrylic polymer particles, or to cross-link adjacent polyacrylic polymer molecules, and to enlarge the polyacrylic polymer particles.

21. A method of increasing the size of water-absorbent cross-linked polyacrylic polymer particles selected from the group consisting of polyacrylic acid; partially neutralized polyacrylic acid; fully neutralized polyacrylic acid; and mixtures thereof, having a size, prior to treatment, of less than about 300 μm comprising:

contacting the surface of the polyacrylic polymer particles with a solution containing a polyfunctional cross-linking agent capable of cross-linking said polyacrylic polymer;

wherein the solution is surface coated onto the cross-linked polyacrylic polymer particles in a weight ratio of polyacrylic polymer, dry basis, to coating solution in the range of about 1:0.01 to about 1:0.5;

subjecting the coated polyacrylic polymer particles to conditions sufficient to react the cross-linking agent with the surface of the polyacrylic polymer particles to form a polyacrylic polymer having enhanced water absorbance; and mixing the coated and dried polyacrylic polymer particles with water after reaction of the surface of the polyacrylic polymer particles with the cross-linking agent, in a weight ratio of polymer particles, dry basis, to water in the range of about 1:1 to about 1:10 to form a paste; drying the paste to a moisture content less than about 15% by weight; and pulverizing the dried paste to form polyacrylic polymer particles having a size greater than the size of the particles prior to the surface cross-linking reaction.

22. A method according to claim 21, further including the step of pulverizing the polyacrylic polymer particles to a desired particle size distribution after cross-linking of the polyacrylic polymer with the solution of cross-linking agent.

23. A method according to claim 1, wherein the polyacrylic polymer is polyacrylic acid neutralized at least 50 mole percent.

24. A method according to claim 1, wherein the polyacrylic polymer is polyacrylic acid neutralized 70 to 100 mole percent.

25. A method according to claim 21, wherein after pulverizing the cross-linked polyacrylic polymer, the particles do not separate into smaller particles upon hydration.

26. A method according to claim 21, wherein the polyacrylic polymer particles containing cross-linking agent on their surfaces are heated to a temperature sufficient to cross-link the surface of adjacent polyacrylic polymer particles, and to dry the particles to a moisture content of about 15% by weight or less, based on the dry weight of the polymer particles.

27. A method according to claim 26 wherein the polyacrylic polymer paste is dried to a degree sufficient to form a polyacrylic polymer sufficiently brittle to be pulverized.

\* \* \* \* \*